(12) United States Patent
Wang et al.

(10) Patent No.: US 7,015,690 B2
(45) Date of Patent: Mar. 21, 2006

(54) OMNIDIRECTIONAL EDDY CURRENT PROBE AND INSPECTION SYSTEM

(75) Inventors: Changting Wang, Schenectady, NY (US); Yuri Alexeyevich Plotnikov, Niskayuna, NY (US); Shridhar Champaknath Nath, Niskayuna, NY (US); William Stewart McKnight, Hamilton, OH (US); Gigi Olive Gambrell, West Chester, OH (US)

(73) Assignee: General Electric Company, Niskayuna, NY (US)

( * ) Notice: Subject to any disclaimer, the term of this patent is extended or adjusted under 35 U.S.C. 154(b) by 29 days.

(21) Appl. No.: 10/856,381

(22) Filed: May 27, 2004

(65) Prior Publication Data

US 2005/0264284 A1 Dec. 1, 2005

(51) Int. Cl.
*G01N 27/90* (2006.01)
*G01N 27/72* (2006.01)

(52) U.S. Cl. ..................... 324/240; 324/243; 324/260
(58) Field of Classification Search ................ 324/232
See application file for complete search history.

(56) References Cited

U.S. PATENT DOCUMENTS

| | | | |
|---|---|---|---|
| 3,437,918 A | 4/1969 | Arnelo | |
| 3,875,502 A | 4/1975 | Neumaier | |
| 4,310,821 A | 1/1982 | Frances | |
| 4,706,020 A | 11/1987 | Viertl et al. | |
| 5,047,719 A | 9/1991 | Johnson et al. | |
| 5,182,513 A | 1/1993 | Young et al. | |
| 5,262,722 A | 11/1993 | Hedengren et al. | |
| 5,315,234 A | 5/1994 | Sutton, Jr. et al. | |
| 5,371,461 A | 12/1994 | Hedengren | |
| 5,371,462 A | 12/1994 | Hedengren et al. | |
| 5,389,876 A | 2/1995 | Hedengren et al. | |
| 5,442,286 A | 8/1995 | Sutton, Jr. et al. | |
| 5,463,201 A | 10/1995 | Hedengren et al. | |
| 5,659,248 A | 8/1997 | Hedengren et al. | |
| 5,793,206 A | 8/1998 | Goldfine et al. | |
| 5,801,532 A | 9/1998 | Patton et al. | |
| 5,831,431 A * | 11/1998 | Gottfried-Gottfried et al. | .. 324/239 |
| 5,903,147 A | 5/1999 | Granger, Jr. et al. | |
| 5,966,011 A | 10/1999 | Goldfine et al. | |

(Continued)

FOREIGN PATENT DOCUMENTS

EP     0512796     8/1997

(Continued)

OTHER PUBLICATIONS

EP Search Report, EP05253068, Jul. 22, 2005.

*Primary Examiner*—Bot LeDynh
(74) *Attorney, Agent, or Firm*—Penny A. Clarke; Patrick K. Patnode

(57) ABSTRACT

An omnidirectional eddy current (EC) probe includes at least one EC channel having a first and a second sense coil that are offset in a first (x) and a second (y) direction and overlap in at least one of the directions (x,y). At least one drive coil is configured to generate a probing field for the EC channel in a vicinity of the sense coils. An omnidirectional EC inspection system includes an omnidirectional EC array probe (ECAP) that includes a number of EC channels and drive coils. Each EC channel includes first and second sense coils with opposite polarities. The drive coils have alternating polarities. Electrical connections perform differential sensing for respective EC channels. Corrective drive coils are disposed at respective ends of the EC channels and generate probing fields. An eddy current instrument is connected to the omnidirectional ECAP and receives differential sensing signals from the EC channels.

19 Claims, 5 Drawing Sheets

U.S. PATENT DOCUMENTS

| | | |
|---|---|---|
| 6,188,218 B1 | 2/2001 | Goldfine et al. |
| 6,344,739 B1 | 2/2002 | Hardy et al. |
| 6,414,483 B1 | 7/2002 | Nath et al. |
| 2005/0007106 A1 * | 1/2005 | Goldfine et al. ............ 324/228 |

FOREIGN PATENT DOCUMENTS

| | | |
|---|---|---|
| GB | 2262607 | 6/1993 |
| WO | 0047986 | 8/2000 |

* cited by examiner

OMNIDIRECTIONAL EDDY CURRENT PROBE AND INSPECTION SYSTEM

BACKGROUND OF THE INVENTION

The present invention relates generally to eddy current inspection and, more specifically, to eddy current probes for non-destructive testing of conductive materials.

Eddy current inspection is a commonly used technique for non-destructive testing of conductive materials for surface flaws. Eddy current inspection is based on the principle of electromagnetic induction, wherein a drive coil carrying currents induces eddy currents within a test specimen, by virtue of generating a primary magnetic field. The eddy currents so induced in turn generate a secondary magnetic field, which induces a potential difference in the sense coils, thereby generating signals, which may be further analyzed for flaw detection. In the case of a flaw in the test specimen, as for example, a crack or a discontinuity, the eddy current flow within the test specimen alters, thereby altering the signals induced in the sense coils. This deviation in the signals is used to indicate the flaw.

Generally, coils that are relatively small in size (for example on the order of about 0.1 to 1.0 mm in length) are used to achieve high resolution. For example, U.S. Pat. No. 5,315,234, Sutton, Jr. et al., entitled "Eddy current device for inspecting a component having a flexible support with a plural sensor array," uses several sensing coils connected in series for sensing small flaws. The voltage output of this configuration relies on a signal difference from two differential sensing coils. Since the coils are made as identical as possible, external electromagnetic noise is eliminated. Another advantage of the differential sensor is its attenuation of the noise associated with small lift-off variations.

However, the eddy current probes described above are limited in their utility by the fact that a prior knowledge of crack orientation is required. Due to this directionality of differential eddy current probes, if more than one flaw orientation is anticipated, the test specimen must be repeatedly scanned in different orientations to detect the flaws. The repeated scanning makes this process laborious and time consuming.

Accordingly, it would be desirable to have an improved eddy current probe and inspection system for detecting cracks and other linear flaws with random orientations. In addition, it would be desirable for the improved eddy current probe to have a large coverage area and be sensitive to both small and long defects in the test specimen.

BRIEF DESCRIPTION

Briefly, in accordance with one embodiment of the present invention, an omnidirectional eddy current (EC) probe includes at least one EC channel, which has a first sense coil and a second sense coil that ate offset from one another in a first (x) and a second (y) direction and overlap one another in at least one of the first and second directions (x,y). At least one drive coil is provided. The drive coil is configured to generate a probing field for the EC channel in a vicinity of the first and second sensing coils.

In accordance with another embodiment of the present invention, an omnidirectional EC array probe (ECAP) includes a number of EC channels. Each of the EC channels includes a first and a second sense coil, which have opposite polarities. A number of drive coils are provided. At least one drive coil is configured to generate a probing field for each of the EC channels in a vicinity of the first and second sensing coils. The drive coils have alternating polarity with respect to neighboring drive coils. Electrical connections operatively connect the first and second sense coils within each of the respective EC channels.

An omnidirectional EC inspection system includes an omnidirectional EC array probe (ECAP) that has a number of EC channels, a number of drive coils, electrical connections that are configured to perform differential sensing for respective EC channels, and a pair of corrective drive coils. One corrective drive coil is disposed at one end of the EC channels. The other corrective drive coil is disposed at another end of the EC channels. Each of the corrective drive coils is configured to generate a probing field. The omnidirectional EC inspection system further includes an eddy current instrument connected to the omnidirectional ECAP and configured to receive a number of differential sensing signals from the EC channels.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
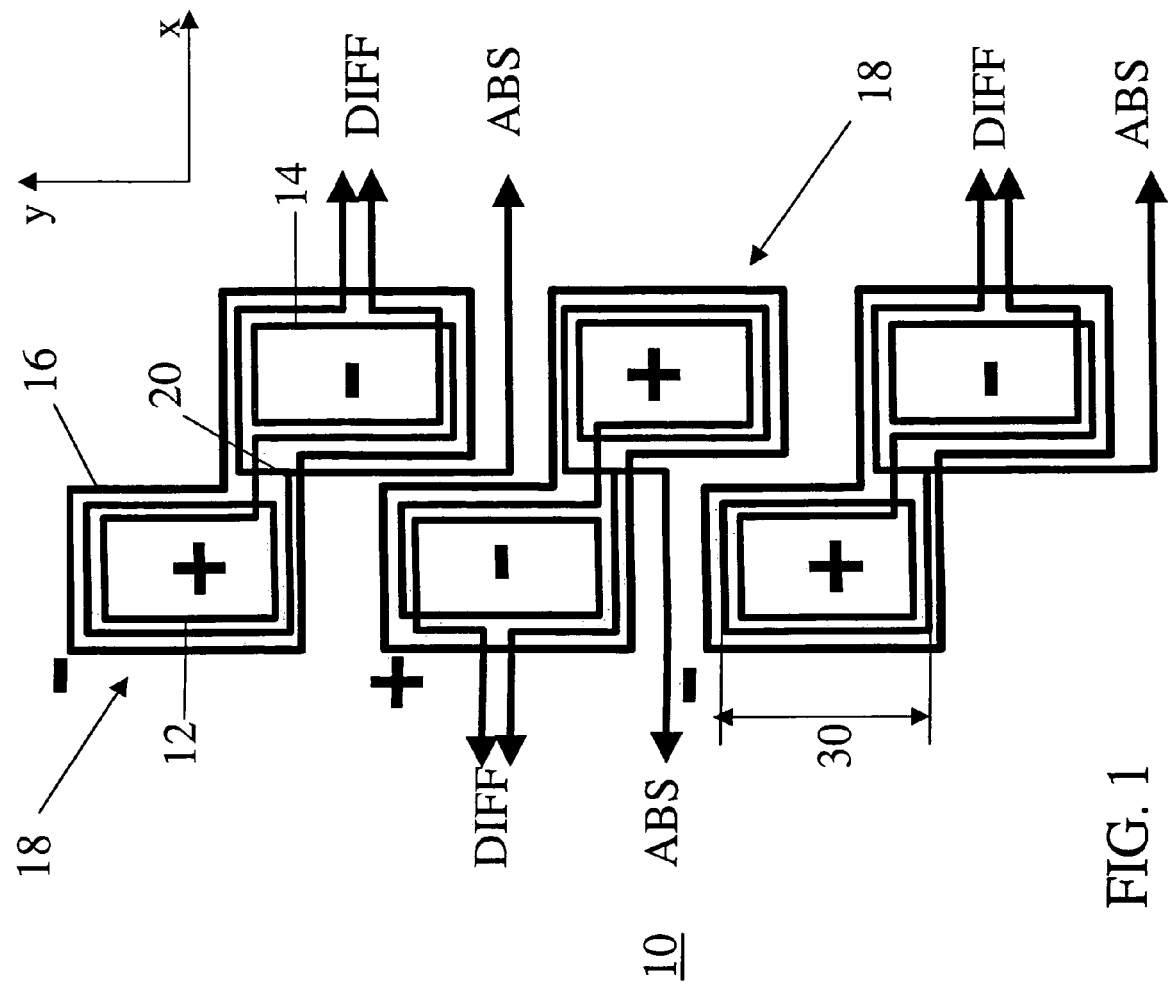
FIG. 1 illustrates an omnidirectional eddy current (EC) probe embodiment of the invention.

FIG. 1 illustrates an omnidirectional eddy current (EC) probe 10 embodiment of the invention. As shown in FIG. 1, the omnidirectional EC probe 10 includes at least one eddy current (EC) channel 18. The EC channel 18 includes a first sense coil 12 and a second sense coil 14. As shown, first and second sense coils 12, 14 are offset from one another in a first (x) and a second (y) direction and overlap one another in at least one of the first and second directions (x,y). As used herein, the terms "offset" and "overlap" are not mutually exclusive. For example, the exemplary first and second sense coils 12, 14 in FIG. 1 are both offset and overlap in the y direction. In other words, for this configuration, the first and second sense coils 12, 14 are partially offset in the y direction, whereas they are completely offset (no overlap) in the x direction. According to a specific embodiment, the first and second sense coils 12, 14 overlap in the second direction y by at least about twenty-five percent (25%) of a length 30 of the sense coils 12, 14. According to a more particular embodiment, the first and second sense coils 12, 14 overlap in the second direction y by at least about thirty-three percent (33%) of the length 30 of the sense coils 12, 14. To provide additional overlap, for another embodiment, the first and second sense coils 12, 14 overlap in the second direction y by at least about fifty percent (50%) of the length 30 of sense coils 12, 14.

As is also shown in FIG. 1, the omnidirectional EC probe 10 further includes at least one drive coil 16 that is configured to generate a probing field for the EC channel 18 in a vicinity of the first and second sensing coils 12, 14. For the exemplary embodiment of FIG. 1, drive coil 16 extends around the first and second sense coils 12, 14 forming the respective EC channel 18.

The omnidirectional EC probe 10 is used for detecting surface or near surface cracks (surface connected flaws) in conductive components, for example in components of aircraft engines, such as disks, spools and blades. Exemplary components are formed of nickel alloys and titanium alloys. The invention, however, is applicable to a variety of conductive components, and these specific components and materials are only examples thereof.

Operationally, the drive coil 16 excites and generates a magnetic flux (probing field). The magnetic field influx into a conductive test object (not shown in FIG. 1) generates an eddy current on the surface of the test object, which in turn generates a secondary magnetic field. In case of a surface flaw (not shown), the secondary magnetic field deviates from its normal orientation when no flaw is present, to a direction corresponding to the flaw orientation. This deviant secondary magnetic field induces corresponding signals (sense signals) in the sense coils 12, 14 thereby indicating the presence of the surface flaw. Because of the offset in two directions (x and y), the differential couple of sense coils 12, 14 advantageously detects the directional deviation in the secondary magnetic flux corresponding to any crack orientation, thereby imparting an omnidirectional sensitivity to the EC probe 10. In addition, the overlap of the sense coils in the y direction provides complementary sensing while scanning the surface of a test object with the probe in the first direction x.

For the exemplary embodiment shown in FIG. 1, the first sense coil 12 has a positive polarity, and the second sense coil 14 has a negative polarity. The exemplary omnidirectional EC probe 10 further includes electrical connections 20 operatively connecting the first and second sense coils 12, 14. For the exemplary embodiment of FIG. 1, the electrical connections 20 are configured to perform both differential sensing (indicated by "DIFF") and absolute sensing (indicated by "ABS"). Beneficially, the inclusion of both differential and absolute sensing features facilitates the detection of both small and long cracks.

To scan a relatively large surface area, it is beneficial to employ an array of EC channels 18. Accordingly, the exemplary omnidirectional EC probe 10 depicted in FIG. 1 includes a number of EC channels 18 and a number of drive coils 16. At least one drive coil 16 is provided for each of the EC channels 18, and for a particular embodiment, one drive coil 16 is provided for each of the EC channels 18. For the particular embodiment of FIG. 4, one drive coil 16 is provided for multiple channels 18. According to a particular embodiment, the omnidirectional EC probe 10 has twenty-four (24) EC channels 18. However, the number of EC channels 18 will depend on both the area being scanned and the instrumentation employed.

As indicated in FIG. 1, the first and second sense coils 12, 14 forming each of EC channels 18 have opposite polarity (indicated by "+" and "−"), and electrical connections 20 operatively connect the first and second sense coils 12, 14 within each of the respective EC channels 18. As shown in FIG. 1, the drive coils 16 have alternating polarity with respect to neighboring drive coils 16 (also indicated by "+" and "−"). Correspondingly, the polarity of the first and second sense coils 12, 14 alternates with respect to neighboring EC channels. For example, the sense coils 12, 14 within the middle EC channel 18 in FIG. 1 have the opposite polarity relative to the sense coils 12, 14 in the upper and lower EC channels 18 in FIG. 1.

Figure 2:
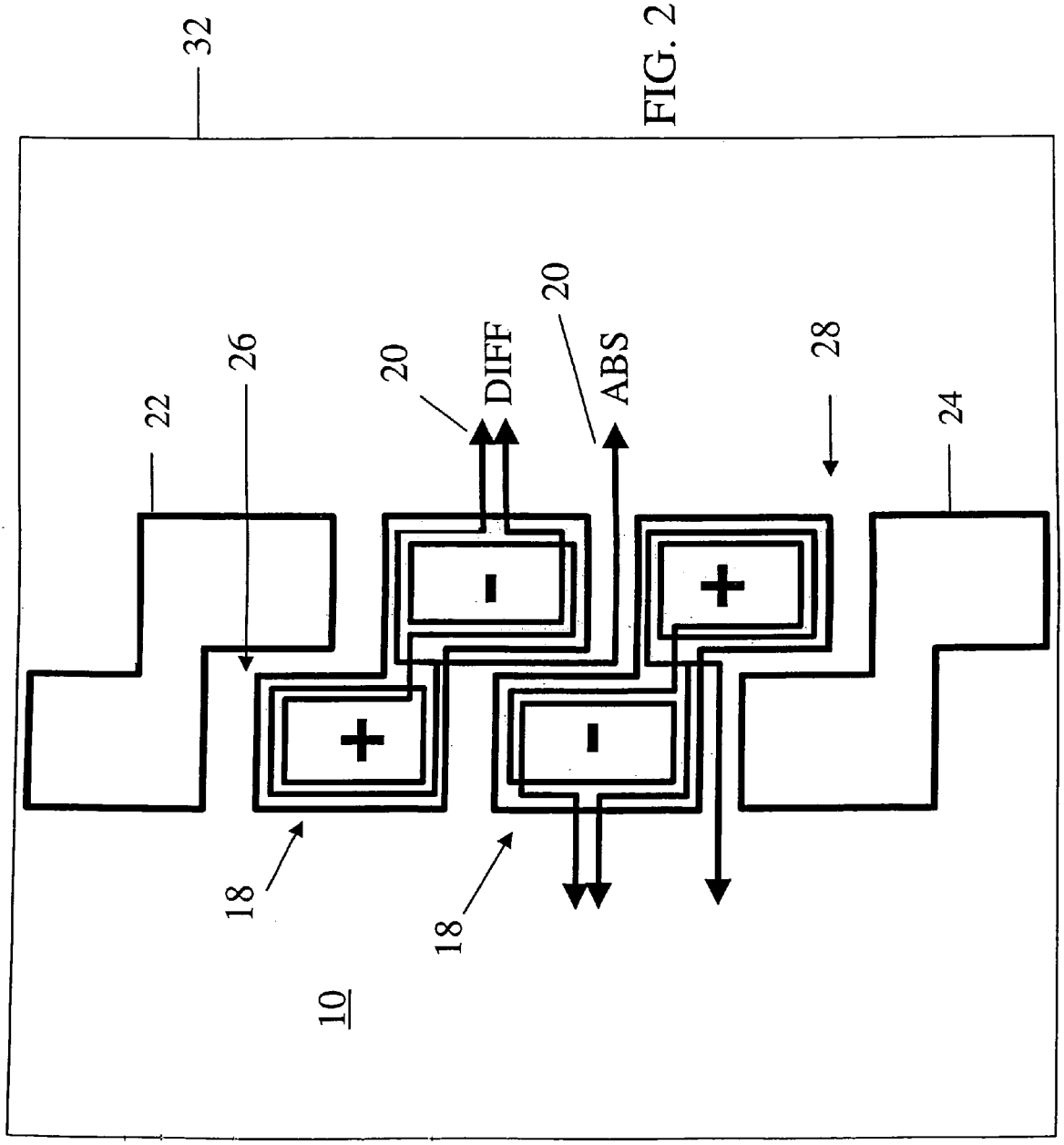
FIG. 2 illustrates an omnidirectional EC probe embodiment of the invention that utilizes corrective drive coils.

In addition to the probing field generated by the drive coil 16 associated with a given EC channel 18, the portion of the test object (not shown) being inspected by the EC channel 18 is also affected by the probing fields of the neighboring drive coils 16. Accordingly, absent any corrective measures, the portions of the test object being inspected by the first and last EC channels 18 in the array would not feel the same probing field as that felt by the intermediate EC channels 18 because each of these EC channels 18 has only one (1) neighboring EC channel 18, whereas each of the other EC channels 18 has two (2) neighboring EC channels. To correct for this imbalance, the omnidirectional EC probe 10 further includes a pair of corrective drive coils 22, 24, according to another embodiment and as shown, for example in FIG. 2. For convenience, the omnidirectional EC probe 10 depicted in FIG. 2 has only two EC channels 18. However, this embodiment may have any number of EC channels 18, for example twenty-four (24) EC channels 18. As shown in FIG. 1, a first one of the corrective drive coils 22 is disposed at a first end 26 of the EC channels 18, and a second one of the corrective drive coils 24 is disposed at a second end 28 of the EC channels 18. Each of the corrective drive coils 22, 24 is configured to generate a probing field. Beneficially, the corrective drive coils 22, 24 improve the sensitivity of the first and last EC channels 18. As indicated in FIG. 2, the electrical connections 20 are configured to perform differential sensing for each of the EC channels 18. In addition, for the embodiment of FIG. 2, the electrical connections 20 are further configured to perform absolute sensing for the EC channels 18.

The multi-channel omnidirectional EC probe 10 described above with reference to FIGS. 1 and 2 is also referred to herein as an omnidirectional EC array probe or ECAP 10. As shown for example in FIG. 2 and according to a particular embodiment, the omnidirectional ECAP 10 further includes a flexible substrate 32. Exemplary flexible substrates are formed of flexible, dielectric substrates, for example flexible organic polymers, such as polyimide, one example of which is marketed under the tradename Kapton®. For the embodiment of FIG. 2, the EC channels 18, the drive coils 16 and the electrical connections 20 are formed on the flexible substrate 32 using known photolithographic methods. A variety of conductive materials, such as copper, silver, and gold can be used. For protection, the EC channels 18, the drive coils 16 and the electrical connections 20 may further be encapsulated on the flexible substrate 32. The flexible substrate 32 is advantageous in that it conforms to irregular reference sample and test object surfaces (not shown in FIGS. 1 and 2), reduces probe wobble and lift-off, and efficiently couples the electromagnetic fields to the test object. According to a particular embodiment, the substrate 32 is relatively thin, for example in a range of about 25–100 $\mu$m, with an exemplary probe being formed on a 25 $\mu$m thick Kapton® substrate.

Figure 3:
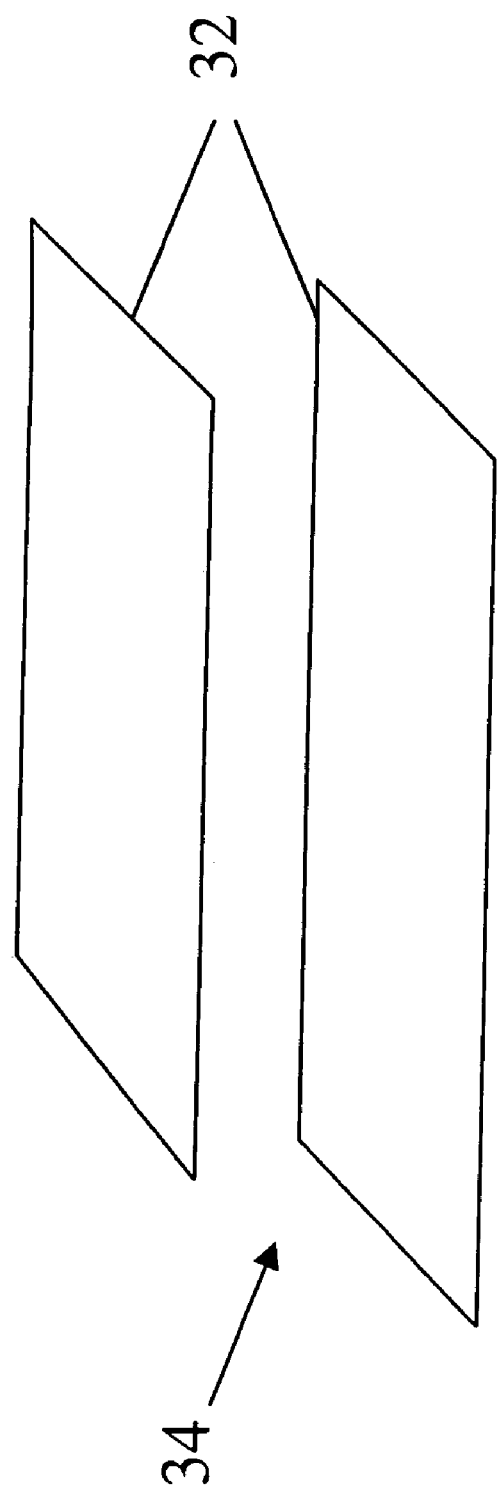
FIG. 3 depicts, in exploded view, an exemplary multi-layer embodiment of an omnidirectional EC probe.

To enhance sensitivity, a multi-layer architecture may also be employed. As schematically depicted in FIG. 3, for this embodiment the omnidirectional ECAP 10 further includes a number of flexible substrates 32 (or a multiple layer substrate 32) arranged in a stack 34, which can be flexible or hard printed circuit board as examples. Although the stack shown in FIG. 3 includes only two layers, the stack 34 may include more layers depending on the desired sensitivity, spatial constraints and specific circuit design. Exemplary layers for the stack 34 of FIG. 3 are shown side-by-side in FIG. 4. As shown for example in FIG. 4, the EC channels 18, drive coils 16 and electrical connections 20 are formed on the flexible substrates 32.

Figure 4:
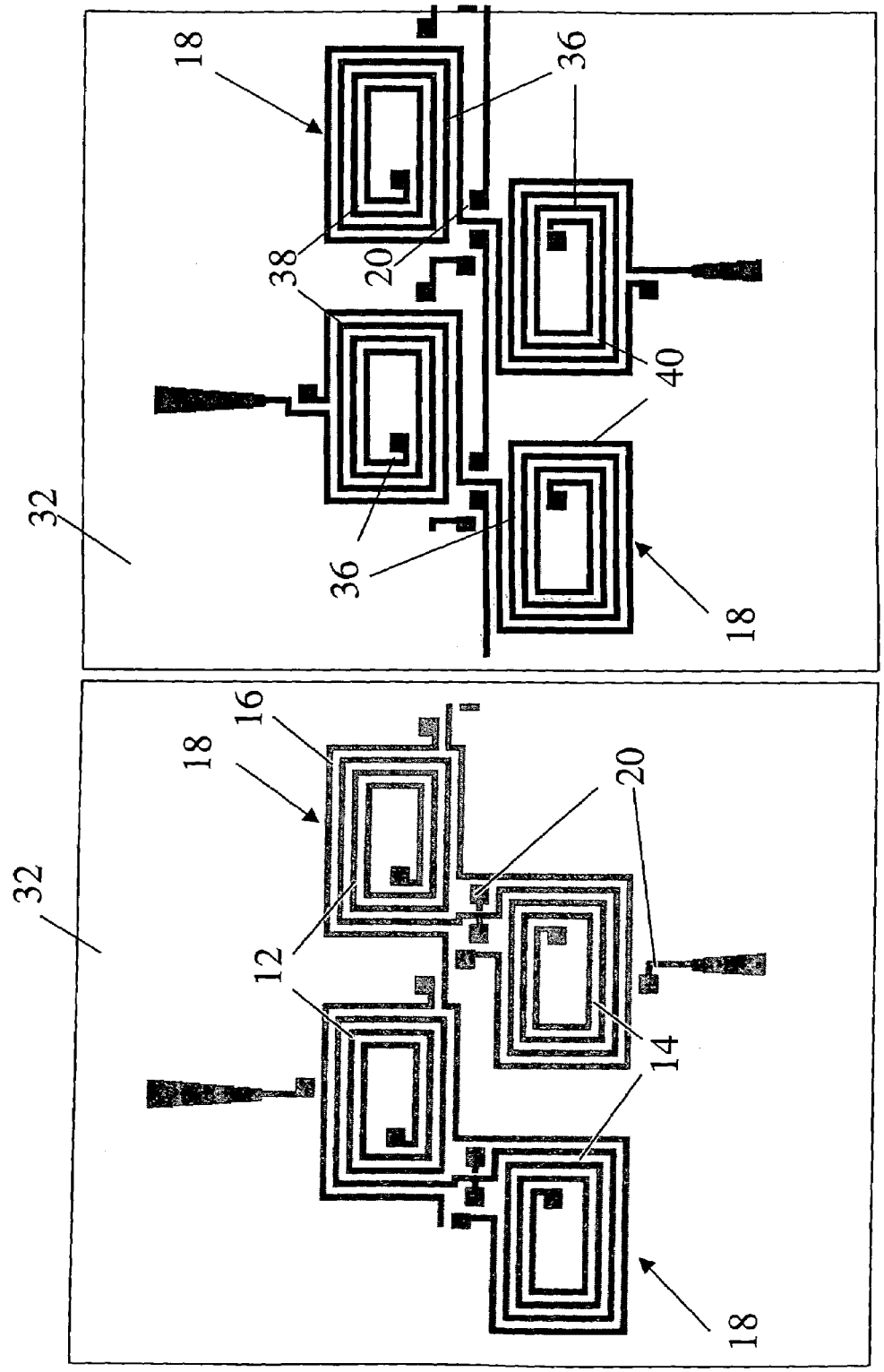
FIG. 4 shows two layers of the omnidirectional EC probe of FIG. 3 side-by-side.

For the exemplary embodiment of FIG. 4, each of the EC channels 18 further includes at least one supplemental pair of sense coils 36. As shown, each of the supplemental pairs of sense coils 36 includes a first supplemental sense coil 38 aligned with the first sense coil 12 and a second supplemental sense coil 40 aligned with the second sense coil 14. Beneficially, the supplemental pairs 36 of sense coils increase the sensitivity of the omnidirectional ECAP 10. According to a particular embodiment, the polarity of the first sense coil 12 coincides with that of the first supplemental sense coil 38. Similarly, for this embodiment, the polarity of the second supplemental sense coil 40 coincides with that of the second sense coil 14. As shown in FIG. 4, the first and second sense coils 12, 14 are disposed on a first one of the flexible substrates 32 (the left substrate 32 in FIG. 4), and the first and second supplemental sense coils 38, 40 are disposed on another one of the flexible substrates 32 (the right substrate 32 in FIG. 4). It should be noted that although both the-sense coils 12, 14 and the supplemental sense coils 38, 40 are depicted as being rectangular, the coils may take other shapes as well. Similarly, the drive coils 16 are not limited to the specific, exemplary rectangular shapes depicted in the figures.

Figure 5:
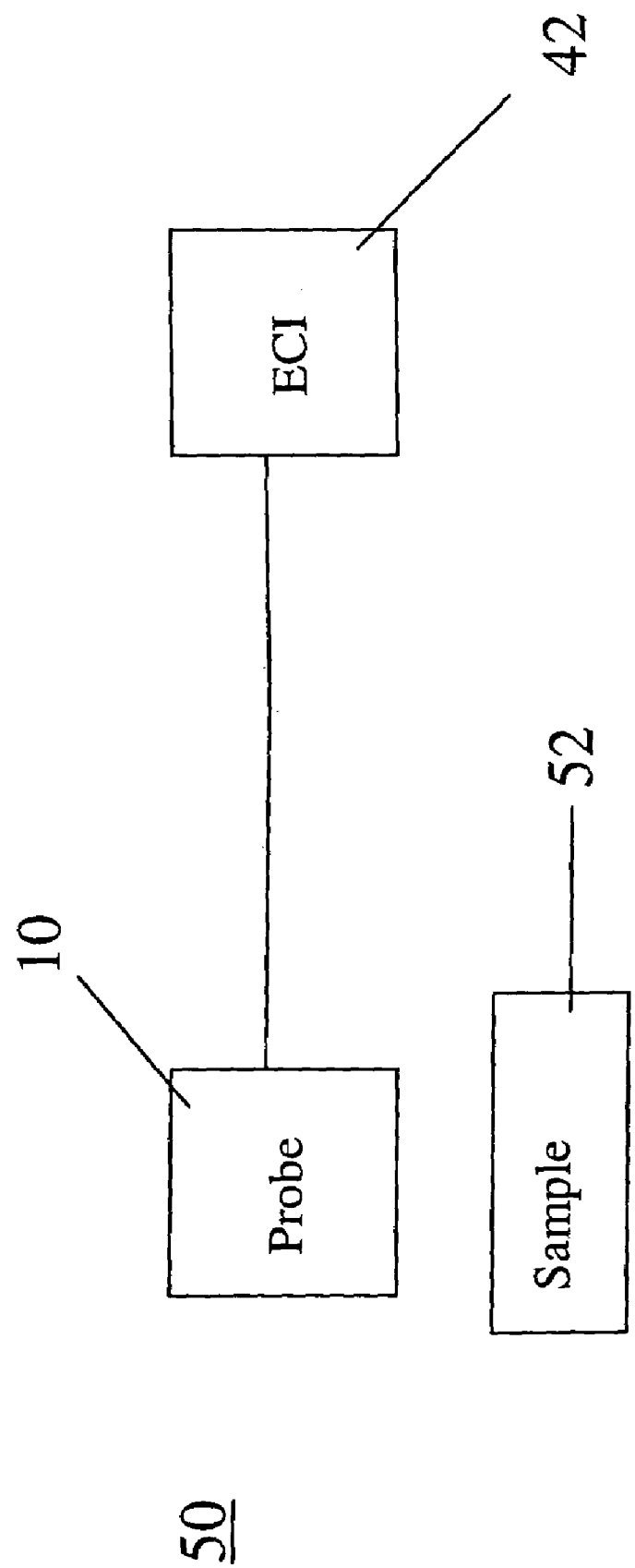
FIG. 5 depicts an omnidirectional EC inspection system embodiment of the invention in block diagram form.

An omnidirectional eddy current (EC) inspection system 50 is described with reference to FIG. 5. As indicated in FIG. 5, the EC inspection system 50 includes an omnidirectional eddy current array probe (ECAP) 10, which is described above with reference to FIGS. 1–4. The omnidirectional ECAP 10 may be a single layer or a multi-layer structure and may be configured for differential and/or absolute sensing. The EC inspection system 50 further includes an eddy current instrument 42 connected to the omnidirectional ECAP 10 and configured to receive a number of sensing signals (differential and/or absolute) from the EC channels 18. Alternatively, the eddy current instrument 42 may be replaced by separate signal generator and comparison modules (not shown) for respectively supplying signals to the drive coils 16 and receiving, comparing and analyzing the sensing signals from the sense coils 12, 14, 38, 40. One exemplary comparison module is a differential amplifier. A computer (not shown) may also be employed to collect and analyze the resulting data, and a display module (not shown) may be used to display the data.

Although only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An omnidirectional eddy current (EC) array probe (ECAP) comprising:
   a plurality of EC channels, each of said EC channels comprising a first sense coil and a second sense coil, wherein said first and second sense coils are offset from one another in a first (x) and a second (y) direction and overlap one another in at least one of the first and second directions (x,y), and wherein said first sense coil has one polarity and said second sense coil has an opposite polarity;
   a plurality of drive coils, wherein at least one drive coil is configured to generate a probing field for each of said EC channels in a vicinity of said first and second sensing coils, and wherein said drive coils have alternating polarity with respect to neighboring drive coils, wherein each of said drive coils extends around said first and second sense coils forming a respective one of said EC channels;
   a plurality of electrical connections operatively connecting said first and second sense coils within each of the respective EC channels; and
   a pair of corrective drive coils, wherein a first one of said corrective drive coils is disposed at a first end of said EC channels, wherein a second one of said corrective drive coils is disposed at a second end of said EC channels, and wherein each of said corrective drive coils is configured to generate a probing field.

2. The omnidirectional ECAP of claim 1 wherein said first and second sense coils overlap in the second direction (y) for at least one of said EC channels.

3. The omnidirectional ECAP of claim 2, wherein said first and second sense coils overlap in the second direction (y) by at least about twenty five percent (25%) of a length of said sense coils for at least one of said EC channels.

4. The omnidirectional ECAP of claim 3, wherein said first and second sense coils overlap in the second direction (y) by at least about thirty-three percent (33%) of the length of said sense coils for at least one of said EC channels.

5. The omnidirectional ECAP of claim 4, wherein said first and second sense coils overlap in the second direction (y) by at least about fifty percent (50%) of the length of said sense coils for at least one of said EC channels.

6. The omnidirectional of claim 1, wherein said electrical connections are configured to perform absolute sensing for each of said EC channels.

7. The omnidirectional ECAP of claim 1, wherein said first and second sense coils overlap in the second direction (y) by at least about twenty five percent (25%) of a length of the sense coils for each of said EC channels.

8. The omnidirectional ECAP of claim 7, wherein said first and second sense coils overlap in the second direction (y) by at least about thirty-three percent (33%) of the length of said sense coils for each of said EC channels.

9. The omnidirectional ECAP of claim 1, wherein said electrical connections are configured to perform differential sensing for each of said EC channels.

10. The omnidirectional ECAP of claim 9, wherein said electrical connections are further configured to perform absolute sensing for at least one of said EC channels.

11. The omnidirectional ECAP of claim 1 further comprising:
    a flexible substrate, wherein said EC channels, said drive coils and said electrical connections are formed on said flexible substrate.

12. The omnidirectional ECAP of claim 1 further comprising:
    a plurality of flexible substrates arranged in a stack, wherein said EC channels, said drive coils and said electrical connections are formed on said flexible substrates.

13. An omnidirectional eddy current (EC) array probe (ECAP) comprising:
    a plurality of EC channels, each of said EC channels comprising a first sense coil and a second sense coil, wherein said first and second sense coils are offset from one another in a first (x) and a second (y) direction and overlap one another in at least one of the first and second directions (x,y), and wherein said first sense coil has one polarity and said second sense coil has an opposite polarity;
    a plurality of drive coils, wherein at least one drive coil is configured to generate a probing field for each of said EC channels in a vicinity of said first and second sensing coils, and wherein said drive coils have alternating polarity with respect to neighboring drive coils;

a plurality of electrical connections operatively connecting said first and second sense coils within each of the respective EC channels; and a plurality of flexible substrates arranged in a stack, wherein said EC channels, said drive coils and said electrical connections are formed on said flexible substrates, wherein each of said EC channels further comprises at least one supplemental pair of sense coils, wherein each of said supplemental pairs of sense coils comprises a first supplemental sense coil aligned with said first sense coil and a second supplemental sense coil aligned with said second sense coil, wherein said first and second sense coils are disposed on a first one of said flexible substrates, and said first and second supplemental sense coils are disposed on another one of said flexible substrates.

14. An omnidirectional eddy current (EC) inspection system comprising:

an omnidirectional eddy current array probe (ECAP) comprising:

a plurality of EC channels, each of said EC channels comprising a first sense coil and a second sense coil, wherein said first and second sense coils are offset from one another in a first (x) direction and overlap one another in a second direction (y), and wherein said first sense coil has one polarity and said second sense coil has an opposite polarity, a plurality of drive coils, wherein at least one drive coil is configured to generate a probing field for each of said EC channels in a vicinity of said first and second sensing coils, and wherein said drive coils have alternating polarity with respect to neighboring drive coils, a plurality of electrical connections operatively connecting said first and second sense coils within each of the respective ones of said EC channels, wherein said electrical connections are configured to perform differential sensing for respective ones of said EC channels, and a pair of corrective drive coils, wherein a first one of said corrective drive coils is disposed at a first end of said EC channels, wherein a second one of said corrective drive coils is disposed at a second end of said EC channels, and wherein each of said corrective drive coils is configured to generate a probing field; and an eddy current instrument connected to said omnidirectional ECAP and configured to receive a plurality of differential sensing signals from said EC channels.

15. The omnidirectional EC inspection system of claim 14, wherein each of said drive coils extends around said first and second sense coils forming a respective one of said EC channels, and wherein said first and second sense coils overlap in the second direction (y) by at least about twenty five percent (25%) of a length of said sense coils for each of said EC channels.

16. The omnidirectional EC inspection system of claim 15, wherein said electrical connections are further configured to perform absolute sensing for at least one of said EC channels, and wherein said eddy current instrument is further configured to receive a plurality of absolute sensing signals from said EC channels.

17. The omnidirectional EC inspection system of claim 15, wherein said omnidirectional ECAP further comprises:

a flexible substrate, wherein said EC channels, said drive coils and said electrical connections are formed on said flexible substrate.

18. The omnidirectional EC inspection system of claim 15, wherein said omnidirectional ECAP further comprises:

a plurality of flexible substrates arranged in a stack, wherein said EC channels, said drive coils and said electrical connections are formed on said flexible substrates.

19. The omnidirectional ECAP of claim 18, wherein each of said EC channels further comprises at least one supplemental pair of sense coils, wherein each of said supplemental pairs of sense coils comprises a first supplemental sense coil aligned with said first sense coil and a second supplemental sense coil aligned with said second sense coil, wherein said first and second sense coils are disposed on a first one of said flexible substrates and said first and second supplemental sense coils are disposed on another one of said flexible substrates.

* * * * *